(12) United States Patent
Atieh et al.

(10) Patent No.: US 8,754,041 B2
(45) Date of Patent: *Jun. 17, 2014

(54) METHOD OF REMOVING E. COLI BACTERIA FROM AN AQUEOUS SOLUTION

(75) Inventors: Muataz Ali Atieh, Dhahran (SA); Amjad Bajes Khalil, Dhahran (SA); Tahar Laoui, Dhahran (SA); Samer Mohammed Al-Hakami, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 446 days.

This patent is subject to a terminal disclaimer.

(21) Appl. No.: 13/075,024

(22) Filed: Mar. 29, 2011

(65) Prior Publication Data

US 2012/0252899 A1   Oct. 4, 2012

(51) Int. Cl.
*A61K 38/04* (2006.01)
*A61K 31/16* (2006.01)
(52) U.S. Cl.
USPC ............. 514/2.8; 514/579; 514/613; 977/746
(58) Field of Classification Search
USPC ............................ 514/579, 2.8, 613; 977/746
See application file for complete search history.

(56) References Cited

U.S. PATENT DOCUMENTS

| | | | |
|---|---|---|---|
| 6,872,681 B2 | 3/2005 | Niu et al. | |
| 7,074,260 B2 | 7/2006 | Lee et al. | |
| 7,413,723 B2 | 8/2008 | Niu et al. | |
| 2006/0027499 A1 | 2/2006 | Ajayan et al. | |
| 2007/0199826 A1 | 8/2007 | Son et al. | |
| 2008/0213367 A1 | 9/2008 | Sarkar et al. | |
| 2010/0050619 A1 | 3/2010 | Colvin et al. | |
| 2010/0075137 A1 | 3/2010 | Sinton et al. | |
| 2010/0086470 A1 | 4/2010 | Mitra et al. | |
| 2010/0203521 A1* | 8/2010 | Klapperich et al. | 435/6 |
| 2010/0256327 A1 | 10/2010 | Yang et al. | |
| 2012/0213663 A1* | 8/2012 | Atieh et al. | 422/21 |

OTHER PUBLICATIONS

Faraz et al., Arabian Journal for Science and Engineering, Section C: Theme Issues (2010), 35(1C), 37-48.*
A. Srivastava, O. N. Srivastava, S. Talapatra, R.Vajtai and P. M. Ajayan, "Carbon Nanotube Filters", *nature materials*, vol. 3, Sep. 2004, Published online: Aug. 1, 2004; doi:10.1038/nmat1192.
Seoktae Kang, Mathieu Pinault, Lisa D. Pfefferle, and Menachem Elimelech, "Single-Walled Carbon Nanotubes Exhibit Strong Antimicrobial Activity", *Langmuir* 2007, 23, 8670-8673.
Jose Rojas-Chapana, Julia Troszczynska, Izabela Firkowska, Christian Morsczeck and Michael Giersig, "Multi-walled carbon nanotubes for plasmid delivery into *Escherichia coli* cells", *Lab Chip*, 2005, 5, 536-539, First published as an Advance Article on the web Mar. 10, 2005.
Matthew W. Marshall, Simina Popa-Nita,and Joseph G. Shapter, "Measurement of functionalised carbon nanotube carboxylic acid groups using a simple chemical process", *Carbon*, vol. 44, Issue 7, Jun. 2006, pp. 1137-1141.

* cited by examiner

*Primary Examiner* — Renee Claytor
*Assistant Examiner* — Shobha Kantamneni
(74) *Attorney, Agent, or Firm* — Richard C Litman

(57) ABSTRACT

The method of removing *Escherichia coli* (*E. coli*) bacteria from an aqueous solution includes the step of mixing multi-walled carbon nanotubes functionalized with a dodecylamine group ($C_{12}H_{27}N$) into an aqueous solution containing *E. coli* bacteria. The multi-walled carbon nanotubes functionalized with a dodecylamine group have an antimicrobial effect against the *E. coli* bacteria. The multi-walled carbon nanotubes may be mixed into the aqueous solution at a concentration of between approximately 0.2 g and 0.007 g of multi-walled carbon nanotubes functionalized with a dodecylamine group per 100 ml of the aqueous solution.

1 Claim, 4 Drawing Sheets

METHOD OF REMOVING E. COLI BACTERIA FROM AN AQUEOUS SOLUTION

BACKGROUND OF THE INVENTION

1. Field of the Invention

The present invention relates generally to disinfection techniques and methods of treating water or aqueous solution for the removal of microorganisms therefrom, and particularly to a method of removing Escherichia coli (E. coli) bacteria from an aqueous solution using carbon nanotubes functionalized with a dodecylamine group ($C_{12}H_{27}N$).

2. Description of the Related Art

Escherichia coli (commonly abbreviated E. coli) is a Gram-negative, rod-shaped bacterium that is commonly found in the lower intestine of warm-blooded organisms (endotherms). Most E. coli strains are harmless, but some, such as serotype O157:H7, can cause serious food poisoning in humans, and are occasionally responsible for product recalls. The harmless strains are part of the normal flora of the gut, and can benefit their hosts by producing vitamin $K_2$ and by preventing the establishment of pathogenic bacteria within the intestine.

Certain strains of E. coli, such as O157:H7, O121 and O104:H21, produce potentially lethal toxins. Food poisoning caused by E. coli is usually caused by eating unwashed vegetables or undercooked meat. O157:H7 is also notorious for causing serious and even life-threatening complications, such as haemolytic-uremic syndrome. This particular strain is linked to the 2006 United States E. coli outbreak due to fresh spinach. Severity of the illness varies considerably. It can be fatal, particularly to young children, the elderly, or the immuno compromised, but is more often mild.

If E. coli bacteria escape the intestinal tract through a perforation (for example from an ulcer, a ruptured appendix, or due to a surgical error) and enter the abdomen, they usually cause peritonitis that can be fatal without prompt treatment. However, E. coli are extremely sensitive to such antibiotics as streptomycin or gentamicin. This, however, could easily change, since E. coli quickly acquires drug resistance. Recent research suggests that treatment with antibiotics does not improve the outcome of the disease, and may, in fact, significantly increase the chance of developing haemolytic-uremic syndrome.

Intestinal mucosa-associated E. coli are also observed in increased numbers in the inflammatory bowel diseases, Crohn's disease, and ulcerative colitis. Invasive strains of E. coli exist in high numbers in the inflamed tissue, and the number of bacteria in the inflamed regions correlates to the severity of the bowel inflammation.

Resistance to beta-lactam antibiotics has become a particular problem in recent decades, as strains of bacteria that produce extended-spectrum beta-lactamases have become more common. These beta-lactamase enzymes make many, if not all, of the penicillins and cephalosporins ineffective as therapy. Extended-spectrum beta-lactamase-producing E. coli are highly resistant to an array of antibiotics, and infections by these strains are difficult to treat. In many instances, only two oral antibiotics and a very limited group of intravenous antibiotics remain effective. In 2009, a gene called New Delhi metallo-beta-lactamase (shortened as NDM-1) that even gives resistance to intravenous antibiotic carbapenem was discovered in India and Pakistan in E. coli bacteria.

Due to the severe nature of E. coli infection and the potential for lethality, it is necessary to develop alternative treatments for E. coli infection and for removal of E. coli bacteria from water and foods. Thus, a method of removing Escherichia coli (E. coli) bacteria from an aqueous solution solving the aforementioned problems is desired.

SUMMARY OF THE INVENTION

The method of removing Escherichia coli (E. coli) bacteria from an aqueous solution includes the step of mixing multi-walled carbon nanotubes functionalized with a dodecylamine group ($C_{12}H_{27}N$) into an aqueous solution containing E. coli bacteria. The multi-walled carbon nanotubes functionalized with a dodecylamine group have an antimicrobial effect against the E. coli bacteria. The multi-walled carbon nanotubes may be mixed into the aqueous solution at a concentration of between approximately 0.2 g and 0.007 g of multi-walled carbon nanotubes functionalized with a dodecylamine group per 100 ml of the aqueous solution.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

As will be described in detail below, the method of removing Escherichia coli (E. coli) bacteria from an aqueous solution includes the step of mixing multi-walled carbon nanotubes doped with a dodecylamine functional group ($C_{12}H_{27}N$) into an aqueous solution containing E. coli bacteria. The multi-walled carbon nanotubes doped with the dodecylamine functional group have an antimicrobial effect against the E. coli bacteria. The multi-walled carbon nanotubes doped with the dodecylamine functional group are preferably mixed into the aqueous solution at a concentration of between approximately 0.2 g and 0.007 g of multi-walled carbon nanotubes doped with the dodecylamine functional group per 100 ml of the aqueous solution.

EXAMPLE

Multi-walled carbon nanotubes (MWCNTs) were purchased from Nanostructured & Amorphous Materials, Inc. of Houston, Tex. The purity of the MWCNTs was greater than 95%, the nanotubes having outer and inner diameters of approximately 10-20 nm and 5-10 nm, respectively. The length of each MWCNT was approximately 10-30 µm. A 300 ml solution of concentrated nitric acid (69% AnalaR Normapur® analytical reagent) was added to 2 g of the MWCNTs. The mixture was refluxed for 48 hours at 120° C.

After cooling to room temperature, the reaction mixture was diluted with 500 ml of de-ionized water and then vacuum-filtered through a filter paper with 3 µm porosity. This washing operation was repeated until the pH became the same as that of de-ionized water, and was followed by drying in a vacuum oven at 100° C.

These conditions led to the removal of catalysts from the MWCNTs and opened both the tube caps, and also formed holes in the sidewalls, followed by oxidative etching along the walls with the concomitant release of carbon dioxide. This relatively non-vigorous treatment minimized the shortening of the tubes, the chemical modification being mostly limited to the opening of the tube caps and the formation of functional groups at defect sites along the sidewalls.

Figure 1:
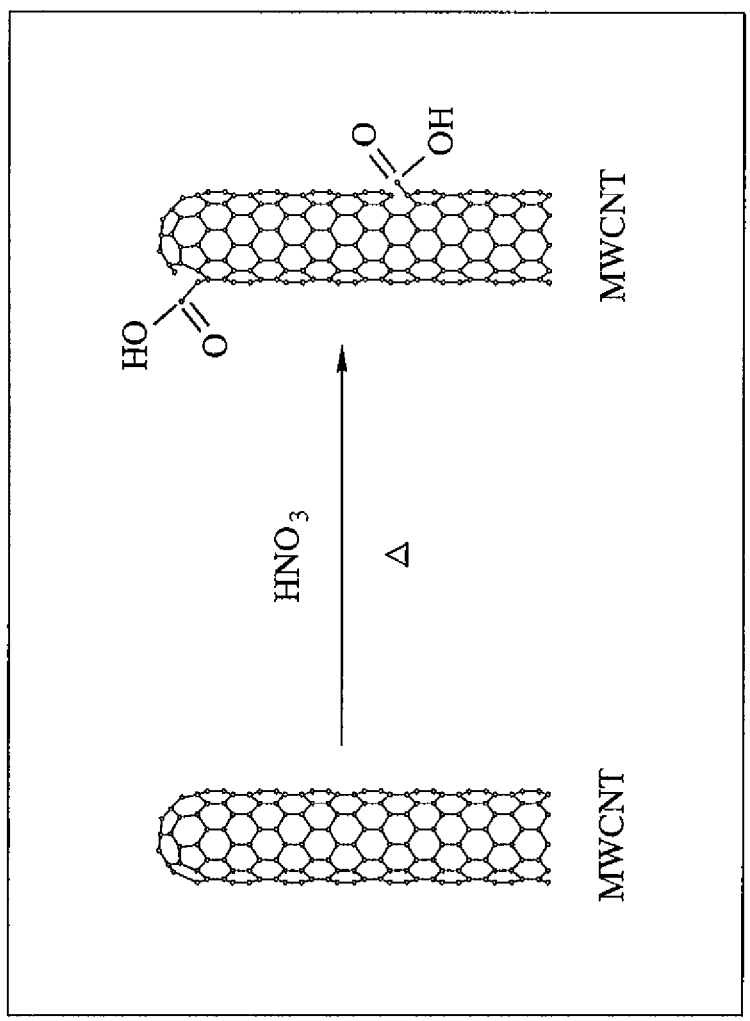
FIG. 1 is a diagram illustrating modification of multi-walled carbon nanotubes to produce multi-walled carbon nanotubes modified with carboxyl groups.

The final products were nanotube fragments whose ends and sidewalls were functionalized with various oxygen containing groups, carboxyl groups being prominent in the formation. FIG. 1 illustrates the chemical modification of the MWCNTs through thermal oxidation to produce the MWCNTs functionalized with carboxyl groups. Further, the percentage of carboxylic functions on the oxidized MWCNT surface did not exceed 4% in the most optimal cases, which corresponds to the percentage of MWCNT structural defects.

Fischer esterification (refluxing a carboxylic acid and an alcohol in the presence of an acid catalyst to produce an ester) is an equilibrium reaction. In order to shift the equilibrium to favor the production of esters, it is customary to use an excess of one of the reactants, typically either the alcohol or the acid. In the present reactions, an excess of the phenol (Aldrich, 98% purity) and 1-oetadecanol (Merck, 97% purity) were used because they are cheaper and easier to remove than the MWCNTs. An alternative method of driving the reaction toward its products is the removal of one of the products as it forms. Water formed in this reaction was removed by evaporation during the reaction.

Figure 2:
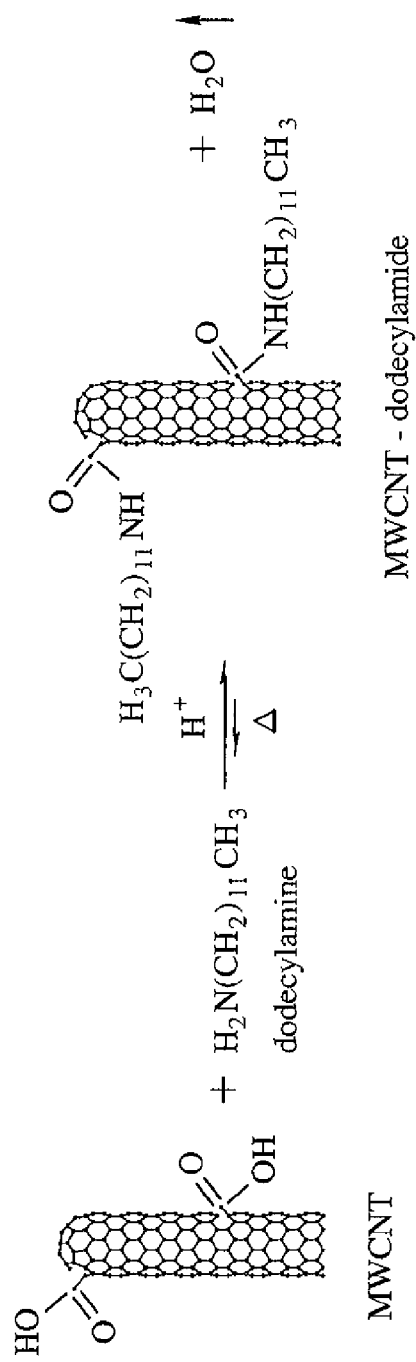
FIG. 2 is a diagram illustrating addition of dodecylamine to the carboxylic group of the modified multi-walled carbon nanotubes of FIG. 1.
Figure 3:
FIG. 3 diagrammatically illustrates multi-walled carbon nanotubes functionalized with carboxylic and dodecylamine groups.

The oxidatively introduced carboxyl groups represent useful sites for further modifications, as they enable the covalent coupling of molecules through the creation of esters, as illustrated in FIGS. 2 and 3. In a 250 ml beaker, 10 g of the material was melted on hotplate at 90° C., and 1 g of MWCNTs was added. The mixture was stirred for 10 minutes, and then a few drops of sulfuric acid (as a catalyst) were added. After addition of the catalyst, the reaction remained on the hotplate and was stirred for two hours.

After completion of the reaction, the mixture was poured into 250 ml of benzene and vacuum-filtered through a filter paper with 3 µm porosity. This washing operation was repeated five times, and was followed by washing with petroleum ether three times and with THF three times. The product was then washed with de-ionized water and acetone a few times, and then the produced functionalized MWCNT material was dried in a vacuum oven at 90° C.

The above particularly involves the activation of the carbonyl group by protonation of the carbonyl oxygen, nucleophilic addition to the protonated carbonyl to form a tetrahedral intermediate, and elimination of water from the tetrahedral intermediate to restore the carbonyl group. Particularly, nucleophilic addition of the amine to the carbonyl group of the protonated acid of the multi-walled carbon nanotubes is followed by elimination of a proton. The tetrahedral intermediate is unstable under the acidic conditions of the reaction and undergoes dehydration to form the amide. The key steps of this reaction involve activation of the carbonyl group by protonation of the carbonyl oxygen, nucleophilic addition to the protonated carbonyl to form a tetrahedral intermediate, and elimination of water from the tetrahedral intermediate to restore the carbonyl group Fourier Transform Infrared Spectroscopy (FTIR) has shown a limited ability to probe the structure of MWCNTs. A factor that has hindered the advancement of FTIR as a tool for MWCNT analysis is the poor infrared transmittance of MWCNTs. A solution to this problem was found through the use of KBr preparations of MWCNT samples. Because of their blackbody characteristics, the MWCNTs have a strong absorbance and often are unable to be distinguished from background noise, thus making it necessary to use a very weak concentration of the MWCNTs in a KBr powder. However, the greater vibrational freedom of attached polymeric species presents much more pronounced peaks, and are thus typically the focus of attention in FTIR results.

Despite this, with very careful sample preparation, some researchers have managed to elucidate peaks corresponding to surface-bound moieties, such as carboxylic acid groups at wavenumbers of 1791, 1203 and 1080 $cm^{-1}$. The spectra of samples were recorded by a Perkin-Elmer 16F PCFT-IR spectrometer. FTIR samples were prepared by grinding dry material into potassium bromide, adding approximately 0.03% wt. This very low concentration of MWCNTs was necessary due to the high absorption of the carbon nanotubes.

Strain $E.$ $coli$ ATCC number 8739 (supplied by the King Fand University of Petroleum and Minerals Clinic) was used. The $E.$ $coli$ was grown overnight in a nutrient broth at 37° C. on a rotary shaker (at 160 rpm). Aliquots of the preculture were inoculated into a fresh medium and incubated in the same conditions to an absorbance of 0.50 at 600 nm. Cells were harvested by centrifugation at 4000 g for 10 min at 4° C., then washed twice with a sterile 0.9% NaCl solution at 4° C., and re-suspended in MWCNTs amine solution to a concentration of $2 \times 10^7$ CFU/ml.

The MWCNTs amine material was sonicated before mixing with the bacterial solution. This material was tested without exposure to any heating source, such as microwave radiation or sunlight. Cultured bacteria (tested bacteria with carbon nanomaterials) was analyzed by plating on nutrient agar plates after serial dilution in 0.9% saline solution. Colonies were counted after 48 hours of incubation at 37° C. Control experiments were carried out in parallel with each experiment performed for the particular MWCNT material tested.

Figure 4:
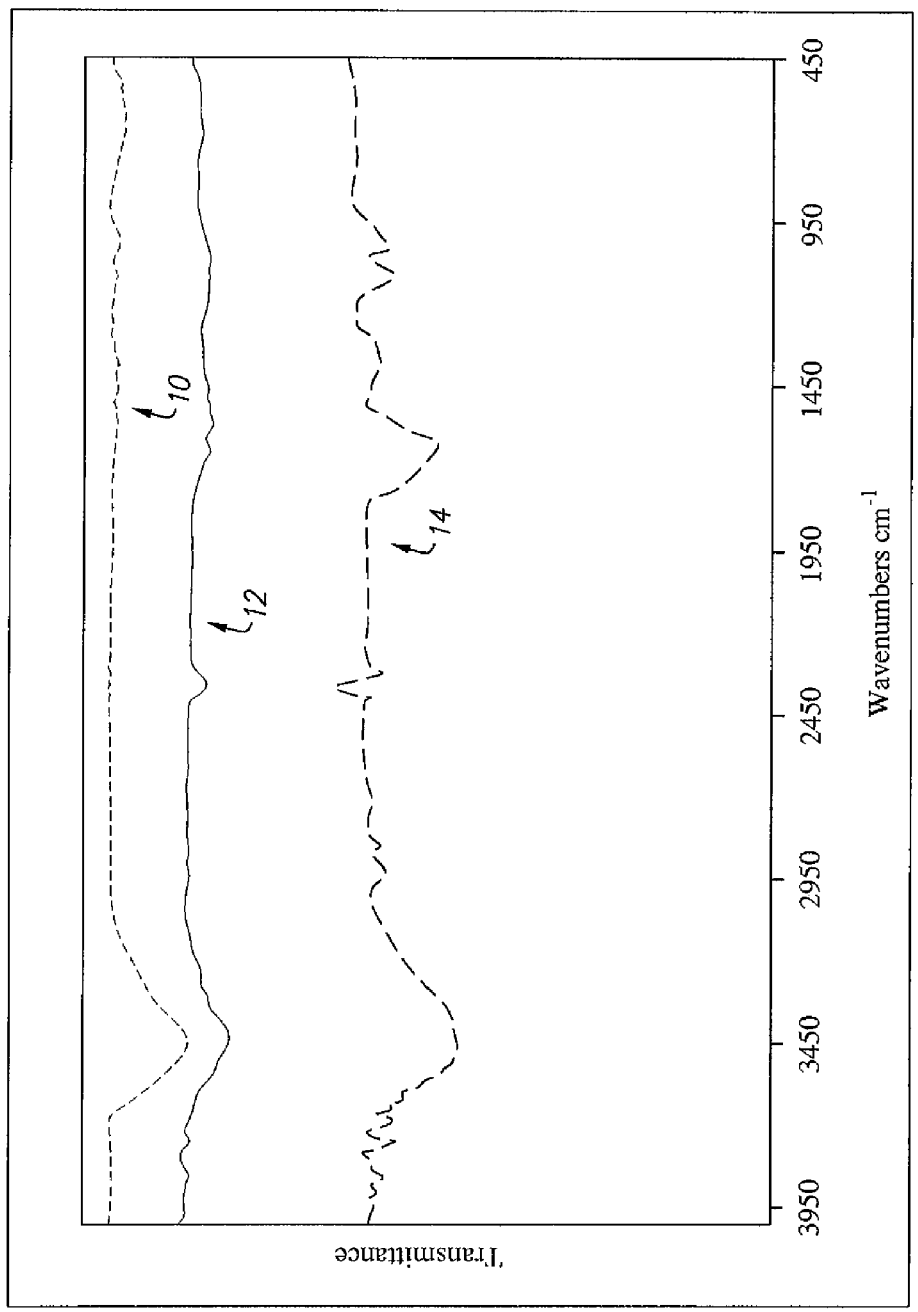
FIG. 4 is a graph showing Fourier transform infrared spectral transmittance plots as functions of wavenumber for multi-walled carbon nanotubes, the COOH-modified multi-walled carbon nanotubes of FIG. 1, and multi-walled carbon nanotubes modified with decylamide.

The untreated and unmodified MWCNTs showed a very weak peak at around 1635 $cm^{-1}$, as shown by line 10 in FIG. 4. This is due to the oscillation of carboxylic groups. This peak moves to 1730 $cm^{-1}$ (associated with the stretch mode of carboxylic groups) observed in the infrared (IR) spectrum of the acid-treated MMWNTs (shown as line 12 in FIG. 4). This indicates that carboxylic groups were formed along with a $C=O$ liaison of the carboxylic acid function due to the oxidation of some carbon atoms on the surface of the MWCNTs by the nitric acid.

The IR spectra of oxidized MWCNTs show four major peaks at 3750, 3450, 2370 and 1562 $cm^{-1}$. The peak at 3750 $cm^{-1}$ is attributed to free hydroxyl groups. The peak at 3445 $cm^{-1}$ is attributed to O—H stretch from carboxylic groups (O=C—OH and C—OH), while the peak at 2364 $cm^{-1}$ is associated with OH stretch from strong H-bond-COOH. The peak at 1565 $cm^{-1}$ is related to the carboxylate anion stretch mode. It should be noted that the unmodified MWCNTs were purified and a part of the catalytic metallic nanoparticles were possibly eliminated during the purification process, cutting the nanotube cap. Thus, the presence of carboxylic groups in these commercial MWCNTs was expected. Moreover, it should be noted that there is no significant difference between the spectra of the samples before and after the $HNO_3$ treatment.

The peak at 1635 cm$^{-1}$ is associated with the stretching of the carbon nanotube backbone. Increased strength of the signal at 1165 cm$^{-1}$ is attributed to C—O stretching in the same functionalities. The peaks around 2877 and 2933 cm$^{-1}$ correspond to the H—C stretch modes of H—C=O in the carboxylic group.

The peak at 2281 cm$^{-1}$ is N—C=O asymmetric vibration (shown as line 14 in FIG. 4), with a new signal peak being observed at 1544 cm$^{-1}$, which is attributed to the overlapping of a signal for N—H, N—C bands and the N—C=O group. Further, each line shows peaks between 1300 and 1100 cm$^{-1}$, which are attributed to the C—C stretch bonds.

Table 1 (below) illustrates the percentage of *E. coli* removal in aqueous solution from the addition of unmodified multi-walled carbon nanotubes and from the addition of multi-walled carbon nanotubes functionalized with a carboxylic (COOH) group. Table 2 illustrates the percentage of *E. coli* removal in aqueous solution from the addition of multi-walled carbon nanotubes functionalized with a dodecylamine group ($C_{12}H_{27}N$). The dosing amount of the MWCNTs during all experiments was fixed at 0.2 g of MWCNTs per 100 ml of NaCl autoclaved solution. For MWCNT-amine, the dosage was varied from approximately 0.2 to 0.007 g per 100 ml.

TABLE 1

*E. coli* removal by MWCNT and MWCNT-COOH

| | Number of *E. coli* Cells | | |
|---|---|---|---|
| Type of MWCNT added to control sample | Control sample | After addition of MWCNTs | % of *E. coli* removal |
| MWCNT (0.2 g/100 ml) | $3.70 \times 10^7$ | $3.50 \times 10^7$ | 5 |
| MWCNT-COOH (0.2 g/100 ml) | $3.70 \times 10^7$ | $3.60 \times 10^7$ | 3 |

TABLE 2

*E. coli* removal by MWCNT-amine ($C_{12}H_{27}N$)

| MWCNT-amine | % of *E. coli* removal |
|---|---|
| 0.2 g/100 ml | 100 |
| 0.07 g/100 ml | 100 |
| 0.05 g/100 ml | 100 |
| 0.03 g/100 ml | 100 |
| 0.012 g/100 ml | 100 |
| 0.007 g/100 ml | 100 |

From Tables 1 and 2, it can be clearly seen that the removal of *E. coli* bacteria from water under the effect of pure MWCNTs and functionalized MWCNTs (with a carboxylic functional group) is relatively minor, with no significant removal. Only 3-5% removal of *E. coli* bacteria was achieved under the effect of MWCNT and MWCNT-COOH, as shown in Table 1.

However, total removal of *E. coli* bacteria was achieved using 0.2 g of MWCNTs functionalized with the amine functional group dodecylamine (denoted as MWCNT-amine in Table 2). Since 0.2 g of MWCNT-amine, which contains only 0.02 g of amine on the surface of the MWCNTs (i.e., 10% of the total weight) removed all bacteria from the aqueous solution, a further reduction of the total weight of the sample (0.2 g) has been carried out to study the effect of the dosage on the removal of *E. coli* bacteria.

A sharp decrease in the weight of the sample from 0.2 to 0.007 g showed that this small weight of MWCNTs-amine, which contains 0.0007 g of amine groups at the surface, also removed all bacteria from the water.

It is to be understood that the present invention is not limited to the embodiments described above, but encompasses any and all embodiments within the scope of the following claims.

We claim:

1. A method of removing *E. coli* bacteria from an aqueous solution, comprising the step of mixing multi-walled carbon nanotubes, the nanotubes having been functionalized with a dodecylamine group ($C_{12}H_{27}N$), into an aqueous solution containing *E. coli* bacteria, wherein the multi-walled carbon nanotubes functionalized with a dodecylamine group have an antimicrobial effect against the *E. coli* bacteria and remove completely the *E. coli* bacteria from the aqueous solution, wherein the multi-walled carbon nanotubes functionalized with the dodecylamine group are mixed into the aqueous solution at a concentration of between approximately 0.2 and 0.007 g per 100 ml of the aqueous solution.

* * * * *